US00PP35618P2

(12) United States Plant Patent
Korlipara

(10) Patent No.: US PP35,618 P2
(45) Date of Patent: Jan. 30, 2024

(54) ***LEUCANTHEMUM* PLANT NAMED 'LEMON MERINGUE'**

(50) Latin Name: ***Leucanthemum* x *superbum***
Varietal Denomination: Lemon Meringue

(71) Applicant: Terra Nova Nurseries, Inc., Canby, OR (US)

(72) Inventor: Harini Korlipara, Tualatin, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 18/128,777

(22) Filed: Mar. 30, 2023

(51) Int. Cl.
*A01H 5/02* (2018.01)
*A01H 6/14* (2018.01)

(52) U.S. Cl.
USPC ..... Plt./285

(58) Field of Classification Search
USPC ..... Plt./263.1, 284, 285
See application file for complete search history.

*Primary Examiner* — Karen M Redden
(74) *Attorney, Agent, or Firm* — The Webb Law Firm

(57) ABSTRACT

A new and distinct *Leucanthemum* plant having double, daisy-type inflorescences, yellow inflorescence buds and young ray florets, and medium-sized fully open inflorescences displaying numerous white ray florets.

2 Drawing Sheets

Botanical classification: *Leucanthemum* x *superbum*.
Varietal denomination: 'Lemon Meringue'.

BACKGROUND OF THE NEW PLANT

The present invention is a new and distinct *Leucanthemum* plant having the varietal name 'Lemon Meringue'. *Leucanthemum* is in the family Asteraceae . 'Lemon Meringue' originated from a controlled cross between unnamed, unpatented, and proprietary *Leucanthemum* x *superbum* seedlings at a nursery in Canby, Oregon.

Compared to *Leucanthemum* plant named 'Bridal Bouquet' (U.S. Plant Pat. No. PP24,260), the new cultivar exhibits more double flowering with yellow coloration when young and has a slightly larger habit. Compared to *Leucanthemum* plant named 'Macaroon' (U.S. Plant Pat. No. PP26,905), the new cultivar is taller and has smaller flowers. Further, when compared to *Leucanthemum* plant named 'Goldfinch' (U.S. Plant Pat. No. PP24,499), the new cultivar is shorter with flowers that shift from yellow to white as they age.

The new variety has only been reproduced by asexual propagation (division and tissue culture). Each of the progeny exhibits identical characteristics to the original plant. Asexual propagation by division and tissue culture using standard micropropagation techniques with terminal and lateral shoots performed in Canby, Oregon shows that the characteristics and distinctions described herein come true to form and are established and transmitted through succeeding propagations. The present invention has not been evaluated under all possible environmental conditions. The phenotype may vary with variations in environment without a change in the genotype of the plant.

When compared to other *Leucanthemum* plants known to the breeder, the new variety is characterized by the following:

1. Double, daisy-type inflorescences;
2. Yellow inflorescence buds and young ray florets;

3. Fully open inflorescences are medium in size and display numerous white ray florets around a yellow-gold disc;
4. Ray florets are linear with lacerated tips giving a more frilled appearance to the inflorescence;
5. Excellent bloom number and excellent rebloom;
6. Medium compact habit, and
7. Excellent vigor.

DESCRIPTION OF THE DRAWINGS

The accompanying photographic drawings illustrate the new variety, with the colors being as nearly true as possible with color illustrations of this type.

DETAILED BOTANICAL DESCRIPTION

Figure 1:
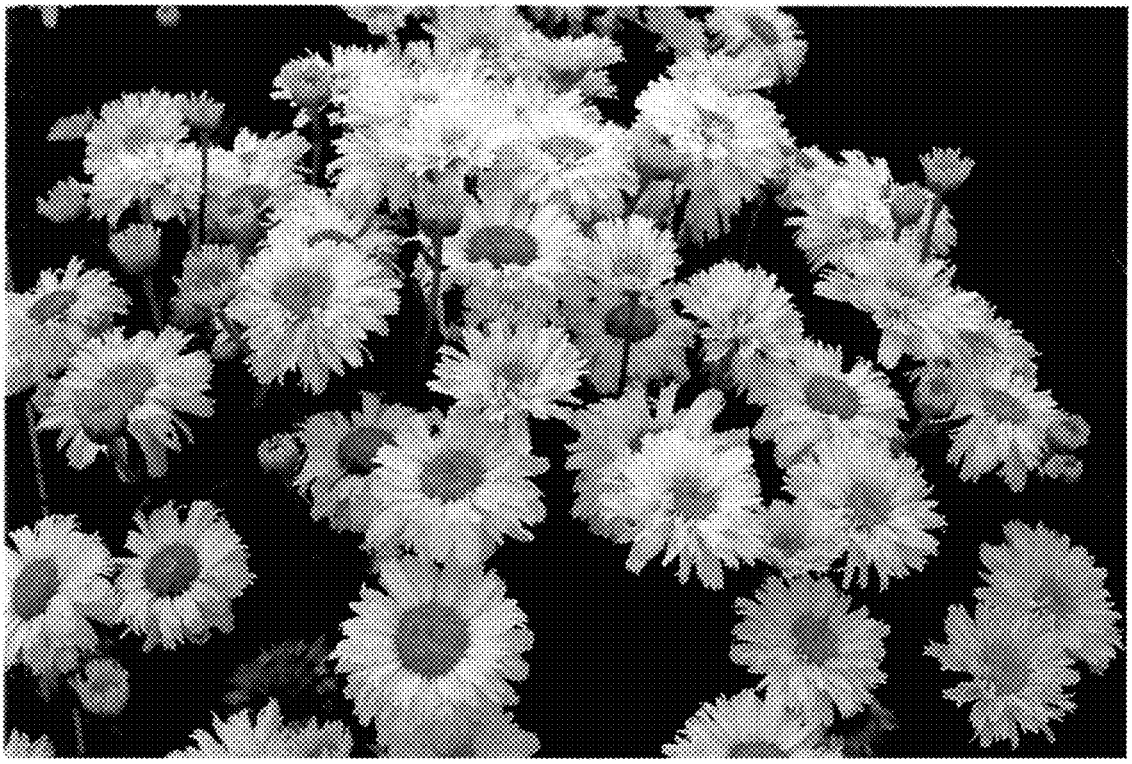
FIG. 1 illustrates a close-up view of a 9-month-old plant of the new variety in Canby, Oregon in July.
Figure 2:
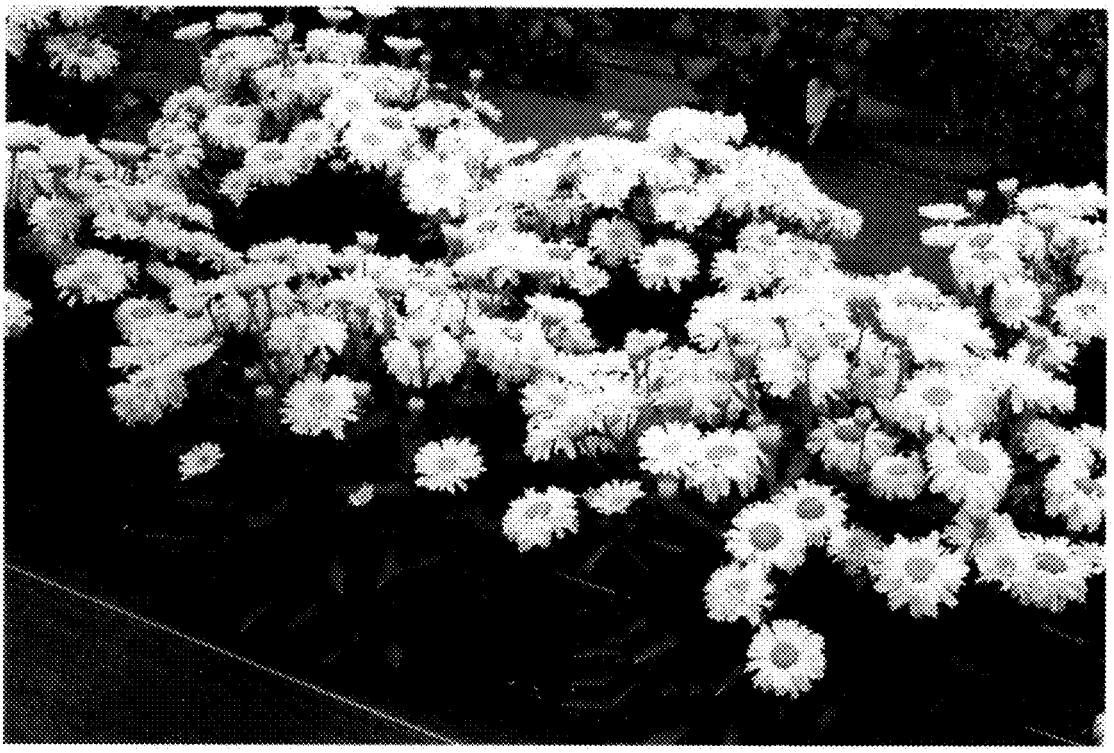
FIG. 2 illustrates 8-month-old plants of the new variety in Canby, Oregon in mid-June.

The following is a detailed description of the new variety based on observations of 10-month-old plants that were grown outside in a field under full sun in Canby, Oregon (USDA Zone 8). Temperatures range from a high of 35° C. in August to a low of 0° C. in January. Normal rainfall in Canby, Oregon is around 1 m per year. Color references are based on the 2007 R.H.S. Colour Chart of The Royal Horticultural Society of London, 5$^{th}$ Edition.

Plant:

*Type.*—Herbaceous perennial.
*Hardiness.*—USDA Zones 5 to 9.
*Size.*—48.0 cm wide and 39.0 cm tall from the top of the soil to the top of the inflorescences.
*Form.*—Basal clump.
*Number of crowns.*—About 56.
*Vigor.*—High.

Flowering stems:

*Type.*—Ascending strongly upright and thick.
*Number.*—About 56 stems from the crown.
*Inflorescences per stem.*—From 1 to 3.

*Size.*—About 39.0 cm tall to a terminal inflorescence and 10.0 cm wide at the base.
*Number of leaves per stem.*—Up to 18, with oldest leaves senescent.
*Strength.*—High.
*Internode length.*—From 1.0 cm to 3.0 cm.
*Texture.*—Pubescent.
*Color.*—RHS 136B.

Leaf:
*Type.*—Simple.
*Arrangement.*—Alternate.
*Shape.*—Lanceolate.
*Length.*—To 7.5 cm.
*Width.*—To 1.75 cm.
*Margin.*—Coarsely serrate.
*Apex.*—Acute.
*Base.*—Clasping.
*Texture.*—Pubescent on both sides.
*Venation.*—Pinnate.
*Upper surface color.*—RHS 137B, with a main vein of RHS 147C.
*Lower surface color.*—RHS 137D, with a main vein of RHS 147D.
*Petiole.*—Sessile.

Inflorescence:
*Type.*—Composite, on terminal stalked heads.
*Flower number.*—About 90 per plant.
*Density.*—High.
*Width.*—To 9.0 cm.
*Depth.*—2.0 cm.
*Form.*—Ray florets hold upright when young, lower ray florets reflex down with maturity, and a mature disc is slightly convex.
*Bloom period.*—June through July in Canby, Oregon.
*Lastingness on the plant.*—About 3 weeks in Canby, Oregon.
*Fragrance.*—Slight to none.
*Fertility.*—Low.

Flower bud (immature inflorescence):
*Form.*—Ray florets held upwards and inner rays cupped inwards.
*Width.*—2.0 cm.
*Depth.*—1.2 cm.
*Color.*—RHS 8B.

Ray florets:
*Number.*—About 90.
*Shape.*—Obelliptic to linear, with from 3 to 5 clefts.
*Length.*—2.5 cm.
*Width.*—0.5 to 0.75 cm.
*Apex.*—Retuse.
*Base.*—Attenuate.
*Margin.*—Entire.
*Texture.*—Glabrous.
*Color* (*both surfaces*).—RHS 8B when young, changing to RHS NN155B.
*Claw.*—To 2.5 mm long and 1.0 mm wide; RHS 150D.
*Pistil.*—1; 3.0 mm long.
*Stamen.*—None.
*Ovary.*—1.0 mm long; RHS 145D.
*Style.*—1.0 mm long; RHS 145C.
*Stigma.*—2-branched; 0.5 mm long; RHS 14B.

Disc/disc florets:
*Disc.*—Shape: Slightly conic, becoming convex. Depth: Tp 13.0 mm. Width: To 18.0 mm. Color: RHS 15B.
*Disc florets.*—Number: About 300. Shape: 5-lobed, tubular campanulate corolla. Length: 4.0 mm. Width: 1.0 mm. Texture: Glabrous. Emerging color: RHS 17B on the top half and RHS 145D on the bottom half. Mature color: RHS NN155A. Pistil: 1; 7.0 mm long. Ovary: 1.0 mm long; RHS 145D. Style: 2.0 mm long; RHS 160B. Stigma: 2-branched; 0.5 mm long; RHS 157C. Stamen: 5; 3.0 mm long. Filament: 1.0 mm long; RHS 150D. Anther: 3.0 mm; RHS 17B. Pollen: None.

Involucral bracts:
*Number.*—About 30 in 3 imbricate whorls.
*Area.*—2.5 cm wide and 10.0 mm deep.
*Lobes.*—Shape: Lanceloate to ovate. Length: 5.0 mm. Width: 6.0 mm. Color: RHS 137B. Margin: Thin; somewhat transparent; RHS 186C. Apex: Acute. Texture: Glabrous.

Receptacle:
*Length.*—17.0 mm.
*Depth.*—4.0 mm.
*Color.*—RHS 149D.

Seeds: None.

Pests/diseases: No unusual resistance or susceptibility noted to date.

I claim:

1. A new and distinct variety of *Leucanthemum* plant named 'Lemon Meringue', substantially as illustrated and described herein.

* * * * *